US010669963B2

(12) United States Patent
Mitsuno et al.

(10) Patent No.: US 10,669,963 B2
(45) Date of Patent: Jun. 2, 2020

(54) ANOMALY DETERMINATION APPARATUS AND CONTROL SYSTEM (71) Applicant: NGK Spark Plug Co., LTD., Nagoya (JP)

(72) Inventors: Junichiro Mitsuno, Konan (JP); Satoru Abe, Ichinomiya (JP); Chihiro Tomimatsu, Kamo-gun (JP); Hidetoshi Makino, Ichinomiya (JP)

(73) Assignee: NGK Spark Plug Co., LTD., Nagoya (JP)

( * ) Notice: Subject to any disclaimer, the term of this patent is extended or adjusted under 35 U.S.C. 154(b) by 65 days.

(21) Appl. No.: 15/956,430

(22) Filed: Apr. 18, 2018

(65) Prior Publication Data
US 2018/0306136 A1    Oct. 25, 2018

(30) Foreign Application Priority Data
Apr. 24, 2017   (JP) ................. 2017-085433

(51) Int. Cl.
*F02D 41/14*        (2006.01)
*G01N 27/417*       (2006.01)
(Continued)

(52) U.S. Cl.
CPC ..... *F02D 41/1495* (2013.01); *F02D 41/1454* (2013.01); *F02D 41/1456* (2013.01);
(Continued)

(58) Field of Classification Search
CPC .... F02D 1/1495; F02D 1/1456; F02D 1/1454; F02D 1/1477; F02D 1/28; F02D 1/281;
(Continued)

(56) References Cited

U.S. PATENT DOCUMENTS 4,252,098 A * 2/1981 Tomczak .................. F01N 3/22
                                                        123/437
5,107,447 A * 4/1992 Ozawa ................. G01R 15/142
                                                        324/536

(Continued)

FOREIGN PATENT DOCUMENTS

JP      2016-114412 A    6/2016

*Primary Examiner* — Dominic E Hawkins
(74) *Attorney, Agent, or Firm* — Leason Ellis LLP (57) ABSTRACT

An anomaly determination apparatus determines an anomaly of a current control apparatus which supplies a control current to a control target and includes a current anomaly determination section. The current anomaly determination section is configured to compare a normal numerical range within which a state quantity changing with the control current falls in a particular state with a particular state quantity which is the state quantity corresponding to the control current generated by the control current generation section in the particular state, and determine that at least one of the reference resistor, the reference current generation section, and the control current generation section is in an anomalous state in the case where the particular state quantity has deviated from the normal numerical range. By using the current anomaly determination section, the anomaly determination apparatus can determine an anomaly of the current control apparatus.

5 Claims, 3 Drawing Sheets

(51) Int. Cl.
*G01N 33/00* (2006.01)
*F02D 41/28* (2006.01)
*G01N 27/04* (2006.01)
*G01N 27/406* (2006.01)
*G01N 27/419* (2006.01)

(52) U.S. Cl.
CPC ......... *F02D 41/1477* (2013.01); *F02D 41/28* (2013.01); *G01N 27/045* (2013.01); *G01N 27/4065* (2013.01); *G01N 27/419* (2013.01); *G01N 27/4175* (2013.01); *G01N 33/007* (2013.01); *G01N 33/0036* (2013.01); *G01N 33/0073* (2013.01); F02D 2041/281 (2013.01)

(58) Field of Classification Search
CPC ............. G01N 33/007; G01N 33/0073; G01N 33/0036; G01N 27/4035; G01N 27/4175; G01N 27/419

See application file for complete search history.

(56) References Cited

U.S. PATENT DOCUMENTS

| | | | |
|---|---|---|---|
| 2007/0032215 A1* | 2/2007 | Oba | H03F 1/0261 |
| | | | 455/313 |
| 2009/0128159 A1* | 5/2009 | Nakatsuji | G01R 31/025 |
| | | | 324/433 |
| 2009/0189580 A1* | 7/2009 | Akahane | H02M 3/156 |
| | | | 323/282 |
| 2014/0188371 A1* | 7/2014 | Miyaji | F02D 41/123 |
| | | | 701/103 |
| 2015/0177209 A1* | 6/2015 | Higuchi | G01N 27/41 |
| | | | 73/23.2 |
| 2016/0169137 A1* | 6/2016 | Higuchi | G01N 33/0036 |
| | | | 702/50 |

* cited by examiner

ANOMALY DETERMINATION APPARATUS AND CONTROL SYSTEM

This application claims the benefit of Japanese Patent Application No. 2017-085433 filed Apr. 24, 2017, which is incorporated herein by reference in its entirety.

FIELD OF THE INVENTION

The present invention relates to an anomaly determination apparatus and a control system which determine an anomaly of a current control apparatus.

BACKGROUND OF THE INVENTION

A known current control apparatus which outputs a control current includes a reference current generation section and a control current generation section.

The reference current generation section generates a reference current through use of, for example, a reference resistor having a predetermined resistance. Specifically, the reference current generation section generates the reference current on the basis of a current which flows through the reference resistor upon application of a predetermined reference voltage thereto.

The control current generation section uses the reference current as a reference to generate a control current which is an integer multiple of the reference current, and supplies the control current to a control target.

Such a current control apparatus is used as, for example, a sensor control apparatus which outputs the control current to a sensor so as to control the sensor (Japanese Patent Application Laid-Open (kokai) No. 2016-114412).

Problem to be Solved by the Invention

However, in the above-described current control apparatus, for example, when the state of connection with the reference resistor becomes anomalous (when wire breakage anomaly, short-circuit anomaly, or the like occurs), the reference current generation section becomes unable to generate an appropriate reference current.

In such a state, since the control current generated on the basis of the reference current assumes an inappropriate value, there arises a problem that the current control apparatus fails to properly control the control target.

In view of the foregoing, an object of the present disclosure is to provide an anomaly determination apparatus and a control system which determine an anomaly of a current control apparatus.

SUMMARY OF THE INVENTION

Means for Solving the Problem

One mode of the present disclosure is an anomaly determination apparatus for determining an anomaly of a current control apparatus which supplies control current to a control target. The anomaly determination apparatus includes a current anomaly determination section.

The current control apparatus includes a reference current generation section and a control current generation section. The reference current generation section is configured to generate a reference current by using a reference resistor. The control current generation section is configured to generate a control current having a predetermined current value while using a current value of the reference current as a reference and supplies the control current to the control target.

The current anomaly determination section is configured to compare a normal numerical range and a particular state quantity and determine that at least one of the reference resistor, the reference current generation section, and the control current generation section is in an anomalous state in the case where the particular state quantity has deviated from the normal numerical range. The normal numerical range is a numerical range at the time of normal within which a state quantity changing with the control current falls in a particular state. The particular state quantity is the state quantity corresponding to the control current generated by the control current generation section in the particular state.

For example, in the case where the state of connection with the reference resistor is in an anomalous state (wire breakage anomaly, short-circuit anomaly, etc.), since the reference resistor and the reference current generation section each enter an anomalous state, a reference current having an appropriate value cannot be generated. In this case, a control current generated by the control current generation section in the particular state (hereinafter referred to as "a particular control current") has an inappropriate value because the particular control current is generated on the basis of the reference current having an inappropriate current value, and the particular control current deviates from the normal range (normal current range) for the particular control current. In the case where the particular control current has an inappropriate value, the particular state quantity which changes with the particular control current also has an inappropriate value, and the particular state quantity deviates from the normal numerical range. Also, even in the case where the reference current generation section can normally generate the reference current having an appropriate value, if the control current generation section is in an anomalous state, the particular control current may have an inappropriate value and deviate from the normal current range. In the case like this where the particular control current has an inappropriate value, likewise, the particular state quantity which changes with the particular control current has an inappropriate value, and the particular state quantity deviates from the normal numerical range.

Therefore, when the comparison between the particular state quantity and the normal numerical range reveals that the particular state quantity has deviated from the normal numerical range, the current anomaly determination section can determine that at least one of the reference resistor, the reference current generation section, and the control current generation section is in an anomalous state.

Therefore, the provision of the current anomaly determination section as described above allows the anomaly determination apparatus to determine an anomaly of the current control apparatus.

Notably, "the state quantity changing with the control current" may be "the control current itself" or may be "voltage, resistance, or the like which changes with the control current." In the case where the state quantity is the control current itself, the particular state quantity can be called a particular control current, and the normal numerical range can be called a normal current range. In such a case, the current anomaly determination section may compare the particular control current and the normal current range and determine that at least one of the reference resistor, the reference current generation section, and the control current generation section is in an anomalous state in the case where the particular control current has deviated from the normal current range.

In the anomaly determination apparatus of the present disclosure, the control target of the current control apparatus may be a sensor provided for an internal combustion engine, and the anomaly determination apparatus may comprise a range setting section which sets the normal numerical range based on an operation state of the internal combustion engine.

Provision of such a range setting section allows the anomaly determination apparatus to set the normal numerical range in the particular operation state and determine that the current control apparatus is anomalous in the case where the particular state quantity has deviated from the normal numerical range. Also, in the case where the anomaly determination apparatus is configured to allow setting of a plurality of particular operation states, the anomaly determination apparatus can set the normal numerical range in accordance with the operation state of the internal combustion engine, and can determine an anomaly of the current control apparatus in various operation states.

The anomaly determination apparatus of the present disclosure may be integrated with the current control apparatus. Since the anomaly determination apparatus of the present disclosure is integrated with the current control apparatus, the determination as to whether or not an anomaly is present in the current control apparatus can be made reliably. Therefore, the anomaly determination apparatus can prevent the current control apparatus from supplying the control current while being in an anomalous state.

The anomaly determination apparatus of the present disclosure may be provided separately from the current control apparatus and include an information receiving section which receives information regarding the particular state quantity from the current control apparatus, and the current anomaly determination section may be configured to perform the determination based on the information received by the information receiving section.

Even in the case where the anomaly determination apparatus is provided separately from the current control apparatus, since provision of the information receiving section allows the anomaly determination apparatus to determine whether or not an anomaly is present in the current control apparatus, the anomaly determination apparatus can prevent the current control apparatus from supplying the control current while being in an anomalous state.

Notably, the current control apparatus may include an information output section which outputs to the outside a piece of control current information representing the control current supplied to the control target. In this case, the anomaly determination apparatus may determine the particular state quantity based on the state quantity information output from the information output section.

Another mode of the present disclosure is a control system comprising a current control apparatus and an anomaly determination apparatus, wherein the anomaly determination apparatus is composed of the above-described anomaly determination apparatus. The current control apparatus includes a reference current generation section which generates a reference current by using a reference resistor, and a control current generation section which generates a control current having a predetermined current value while using a current value of the reference current as a reference and supplies the control current to the control target.

In such a control system, since the determination as to whether or not an anomaly is present in the current control apparatus can be made, it is possible to prevent the current control apparatus from supplying the control current while being in an anomalous state.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Embodiments to which the present disclosure is applied will be described with reference to the drawings.

Notably, needles to say, the present disclosure is not limited to the following embodiments, and various forms may be employed so long as they fall within the technical scope of the present disclosure.

1. First Embodiment 1-1. Overall Configuration

Figure 1:
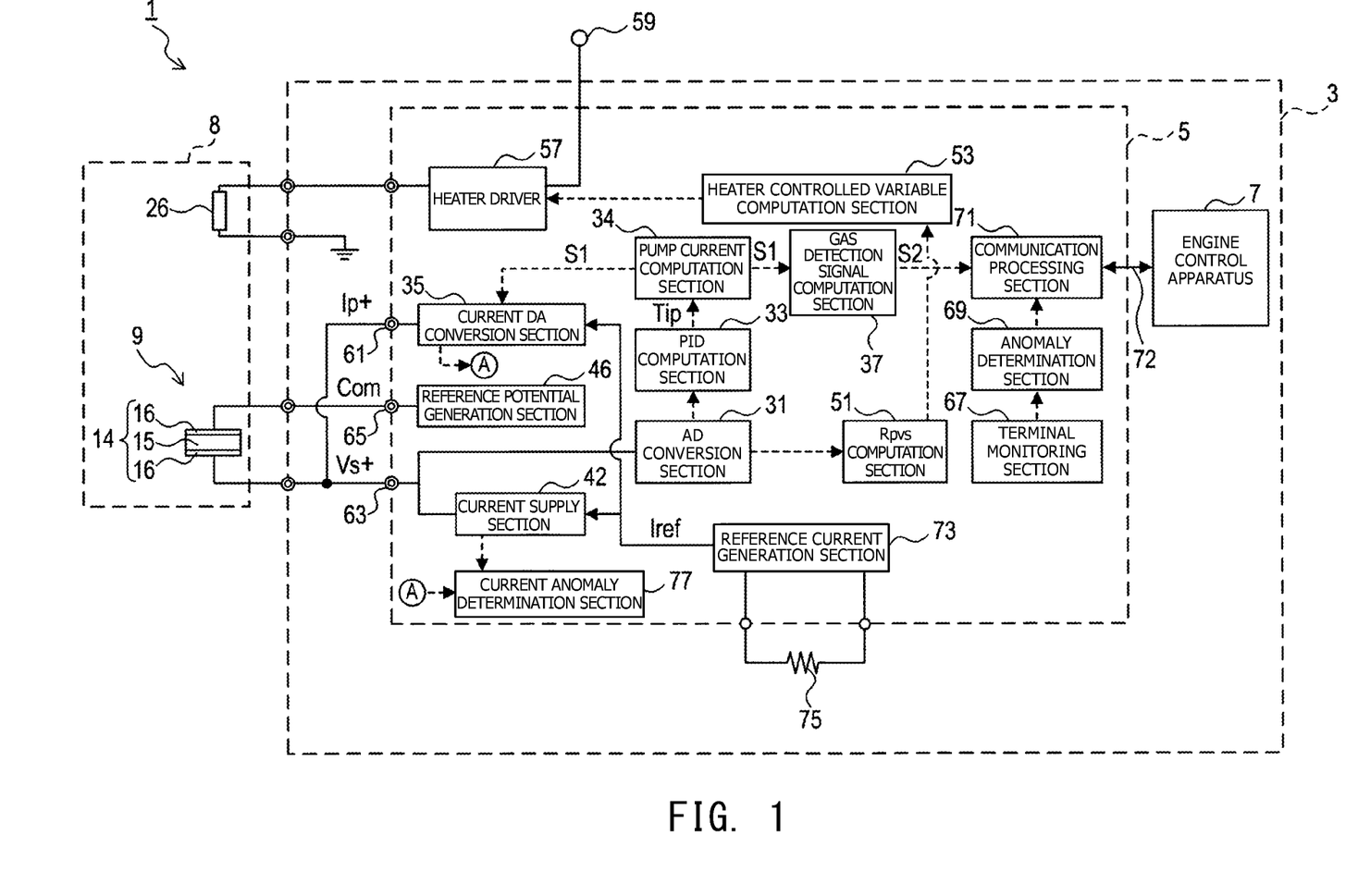
FIG. 1 is an overall diagram of a gas detection system including a sensor control apparatus.

FIG. 1 is an overall diagram of a gas detection system 1 which is an embodiment of the present disclosure.

The gas detection system 1 is used, for example, for the purpose of detecting a particular gas (oxygen in the present embodiment) contained in exhaust gas discharged from an internal combustion engine.

The gas detection system 1 includes a gas detection apparatus 3 and a gas sensor 8.

The gas detection apparatus 3 includes a sensor control apparatus 5 and an engine control apparatus 7.

The sensor control apparatus 5 drives and controls the gas sensor 8 so as to detect the concentration of oxygen in the exhaust gas and communicates the detected oxygen concentration to the engine control apparatus 7. The details of the sensor control apparatus 5 will be described later.

The engine control apparatus 7 is a microcontroller which executes various control processes for controlling the internal combustion engine. As one of the various control processes, the engine control apparatus 7 executes air-fuel ratio control for the internal combustion engine while using the oxygen concentration detected by the sensor control apparatus 5.

The gas sensor 8 is an oxygen sensor for detecting oxygen. The gas sensor 8 is provided on an exhaust pipe of the internal combustion engine and is used to detect the concentration of oxygen in the exhaust gas in a wide range. The gas sensor 8 is also called a linear lambda sensor. The gas sensor 8 is composed of a sensor element 9 and a heater 26.

The sensor element 9 includes a pump cell 14. The pump cell 14 includes an oxygen-ion-conducting solid electrolyte body 15 formed of partially-stabilized zirconia ($ZrO_2$), and a pair of porous electrodes 16 mainly formed of platinum and provided on the front and back surfaces of the solid electrolyte body 15.

The heater 26 includes a heat generation resistor which generates heat when externally energized. The heater 26 is provided in order to heat the sensor element 9 (in particular, the pump cell 14), thereby bringing the sensor element 9 (the pump cell 14) into an activated state (a state in which the sensor element 9 can perform gas detection).

Notably, the sensor element 9 includes a measurement chamber (not shown) and a reference oxygen chamber (not shown) formed therein. One of the paired porous electrodes 16 of the pump cell 14 is exposed to the measurement chamber. The other of the paired porous electrodes 16 is exposed to the reference oxygen chamber. An object gas (exhaust gas in the present embodiment) is introduced from the outside into the measurement chamber through a porous diffusion layer (not shown). The atmospheric air serving as a reference gas is introduced from the outside into the reference oxygen chamber.

The sensor element 9 is an oxygen sensor element which detects the concentration of oxygen by a so-called limit current method. Its output characteristic which represents the relation between application voltage Vp and pump current Ip in the pump cell 14 has a region where a characteristic curve representing the pump current Ip is flat and parallel to the voltage axis; namely, a region of limit current (limit current region) where the pump current Ip is constant. In the flat region (limit current region), even when the application voltage Vp changes, the pump current Ip substantially does not change and remains at a constant level (limit current).

This flat region is a limit current region in which the pump current Ip assumes a value corresponding to the oxygen concentration (namely, air-fuel ratio), and a change in the limit current corresponds to a change in the oxygen concentration. It has been known that the higher the oxygen concentration, the larger the pump current Ip in the limit current region. Therefore, the oxygen concentration in the exhaust gas can be detected by applying an application voltage Vp corresponding to the limit current region to the pump cell 14 of the sensor element 9 and using the pump current Ip obtained as a result of the application of the application voltage Vp. Namely, the limit current of the pump current Ip increases as the oxygen concentration in the exhaust gas increases (as the air-fuel ratio shifts toward the lean side), and the limit current decreases as the oxygen concentration in the exhaust gas decreases (as the air-fuel ratio shifts toward the rich side). Therefore, the oxygen concentration (air-fuel ratio) can be detected on the basis of the limit current.

In the present embodiment, the application voltage Vp is applied to the paired porous electrodes 16 of the pump cell 14 of the sensor element 9 so as to cause the pump current Ip to flow between the paired porous electrodes 16, so that oxygen is pumped by the pump current Ip (for example, oxygen is moved between the measurement chamber and the reference oxygen chamber). As is well known, the oxygen concentration can be detected on the basis of the current value (limit current) of the pumping current Ip at the time when the pumping current Ip during the pumping becomes constant.

Namely, the gas sensor 8 is used for applications in which the concentration of oxygen contained in an object gas (exhaust gas) is detected on the basis of the current value (limit current) of the pumping current Ip at the time when the pumping current during the pumping in the sensor element 9 becomes constant.

1-2. Sensor Control Apparatus

The sensor control apparatus 5 is configured to drive and control the gas sensor 8 so as to detect the concentration of oxygen in the exhaust gas and communicate the detected oxygen concentration to the engine control apparatus 7.

The sensor control apparatus 5 is composed of an ASIC (application specific IC). In FIG. 1, the sensor control apparatus 5 is shown in the form of a functional block diagram.

The sensor control apparatus 5 includes an AD conversion section 31 (an analog-to-digital conversion section 31), a PID computation section 33, a pump current computation section 34, a current DA conversion section 35 (a current digital-to-analog conversion section 35), a gas detection signal computation section 37, a current supply section 42, and a reference potential generation section 46. Also, the sensor control apparatus 5 includes an Rpvs computation section 51, a heater controlled variable computation section 53, and a heater driver 57. Further, the sensor control apparatus 5 includes a pump current terminal 61 (an Ip+ terminal 61), a detection voltage terminal 63 (a Vs+ terminal 63), a reference potential terminal 65 (a COM terminal 65), a terminal monitoring section 67, an anomaly detection section 69, a communication processing section 71, a reference current generation section 73, a reference resistor 75, and a current anomaly determination section 77.

The current supply section 42 supplies various currents to the sensor element 9 (specifically, the pump cell 14) through the detection voltage terminal 63. Examples of the various currents include a pulse current Irpvs for detecting the internal resistance Rpvs of the sensor element 9 (the pump cell 14), etc. The current supply section 42 does not supply these currents at all times but supplies the currents at respective proper timings.

The reference potential generation section 46 sets the potential of the reference potential terminal 65 (the COM terminal 65) to a predetermined potential. Specifically, a potential obtained by adding a reference setting voltage (2.7 V in the present embodiment) to a ground potential GND of the internal combustion engine which serves as a reference is set as the potential of the reference potential terminal 65. Notably, in the present embodiment, the potential of the reference potential terminal 65 corresponds to a reference potential used when the sensor element 9 (the pump cell 14) is controlled.

The AD conversion section 31 detects a voltage across the pump cell 14 (detection voltage Vs) on the basis of the potential of the detection voltage terminal 63 and the potential of the reference potential terminal 65 and converts an analog value representing the detection voltage Vs to a digital value. The AD conversion section 31 communicates the digital value obtained as a result of the conversion to various sections of the sensor control apparatus 5 (for example, the PID computation section 33, the Rpvs computation section 51, etc.).

Notably, when the pump current Ip is input by the current DA conversion section 35, the voltage across the pump cell 14 (the detection voltage Vs) can be utilized as a sensor output signal Vs1 which changes with the oxygen concentration in the measurement chamber. Also, when the pulse current Irpvs is input by the current supply section 42, the voltage across the pump cell 14 (the detection voltage Vs)

can be utilized as a response signal Vs2 which changes with the internal resistance Rpvs of the pump cell 14.

The PID computation section 33 is configured to execute a pump current control process by digital processing. The pump current control process is a control process for controlling the pump current Ip supplied to the pump cell 14 such that the detection voltage Vs (the sensor output signal Vs1) of the pump cell 14 becomes equal to a target control voltage (for example, 450 mV in the present embodiment). The PID computation section 33, which executes the pump current control process, performs PID computation on the basis of the deviation ΔVs of the detection voltage Vs (the sensor output signal Vs1) of the pump cell 14 from the target control voltage (450 mV) and computes a supply control value (target pump current value Tip) used for controlling the supply of the pump current Ip to the pump cell 14 such that the deviation ΔVs approaches zero (in other words, the detection voltage Vs approaches the target control voltage).

The pump current computation section 34 digitally extracts a DAC control signal S1 (a first filtered signal S1) from a digital signal representing the target pump current value Tip computed by the PID computation section 33, by attenuating frequency components whose frequencies are higher than a predetermined first cut-off frequency (100 Hz in the present embodiment).

Since the DAC control signal S1 is a signal obtained by removing (through attenuation) frequency components (noise components) whose frequencies are higher than the first cut-off frequency from the digital signal representing the target pump current value Tip of the pump current Ip, the DAC control signal S1 is a digital signal which represents the target pump current value Tip of the pump current Ip and in which the noise components superimposed as a result of the digital computation at the PID computation section 33 have been attenuated. Therefore, even when the sampling interval of the pump current Ip (the digital signal) is shortened for higher speed operation, an increase in the differential noise component of the pump current Ip can be restrained.

The gas detection signal computation section 37 digitally extracts a gas detection signal S2 (a second filtered signal S2) from the digital signal representing the DAC control signal S1 computed by the pump current computation section 34, by attenuating frequency components whose frequencies are higher than a predetermined second cut-off frequency (50 Hz in the present embodiment).

Since the gas detection signal S2 is a signal obtained by removing (through attenuation) frequency components (noise components) whose frequencies are higher than the second cut-off frequency from the DAC control signal S1, the gas detection signal S2 is a digital signal obtained by further removing (through attenuation) noise components (the noise components superimposed as a result of the digital computation at the pump current computation section 34) from the DAC control signal S1.

Since the DAC control signal S1 is smaller in the number of times of filter processing than the gas detection signal S2, the DAC control signal S1 is a digital signal which represents the target pump current value Tip of the pump current Ip and on which a latest change in the detection voltage Vs of the pump cell 14 is reflected relatively greatly. Since such a digital signal is a signal suitable for feedback control of the pump cell 14, by supplying the pump current Ip produced on the basis of the DAC control signal S1 to the pump cell 14, the pumping (pumping out and pumping in) of oxygen by the pump cell 14 can be performed appropriately in accordance with the latest change in the detection voltage Vs of the pump cell 14. Notably, the DAC control signal S1 is a digital signal containing information regarding the supply control value for the pump current Ip; specifically, information representing a current value and a supply (flow) direction (forward direction or reverse direction) of the pump current Ip specified by the target pump current value Tip.

The current DA conversion section 35 receives the DAC control signal S1 (digital value) computed at the pump current computation section 34 and performs DA conversion for the received DAC control signal S1 and supplies the pump current Ip, which is an analog value obtained through the DA conversion, to the pump cell 14.

Since the gas detection signal S2 is larger in the number of times of filter processing than the DAC control signal S1, the gas detection signal S2 is a digital signal which represents the target pump current value Tip of the pump current Ip and on which a long term change in the detection voltage Vs of the pump cell 14 is reflected relatively greatly. Since such a digital signal is a signal suitable for detection of a particular component (oxygen) contained in the object gas (exhaust gas). Therefore, by using the gas detection signal S2 as a signal for detecting the concentration of oxygen contained in the exhaust gas, it becomes possible to detect the concentration of oxygen contained in the exhaust gas on the basis of the long term change in the detection voltage Vs of the pump cell 14. Thus, the accuracy in detecting the oxygen concentration can be improved.

The communication processing section 71 executes a communication control process for sending various pieces of information to the engine control apparatus 7 and receiving various pieces of information from the engine control apparatus 7 by means of SPI communication (serial peripheral interface commination) through an SPI communication line 72. The communication processing section 71 sends and receives information which includes at least control information regarding sensor control. For example, the communication processing section 71 sends the gas detection signal S2 to the engine control apparatus 7.

Also, the communication processing section 71 has a function of determining whether or not the state of communication with the engine control apparatus 7 is an anomalous state (communication anomaly). The communication processing section 71 resets a communication anomaly flag Fcf (Fcf=0) when the communication processing section 71 determines that the communication state is normal, and sets the communication anomaly flag Fcf (Fcf=1) when the communication processing section 71 determines that the communication state is anomalous. The communication anomaly flag Fcf is one of internal flags used for various control processes performed in the sensor control apparatus 5. The communication processing section 71 sends information to the engine control apparatus 7 after confirming that the communication anomaly flag Fcf is in the reset state.

The engine control apparatus 7 computes the concentration of the particular gas (oxygen in the present embodiment) contained in the exhaust gas on the basis of the gas detection signal S2. Namely, the engine control apparatus 7 computes the concentration of oxygen contained in the object gas on the basis of history data of the pump current Ip caused to flow through the pump cell 14 such that the oxygen concentration within the measurement chamber becomes equal to a predetermined target concentration (for example, an oxygen concentration corresponding to the stoichiometric air-fuel ratio).

Notably, the sensor control apparatus 5 includes an unillustrated EEPROM and an unillustrated RAM. The EEPROM is a storage section which stores the details of the control process, various parameters used for the control process, etc. In addition, the EEPROM stores various pieces of information (the maximum permissible current of the pump cell 14, etc.) which are determined in accordance with the type and characteristics of the gas sensor 8, which is a control target. These pieces of information are stored in the EEPROM in the stage of fabrication of the sensor control apparatus 5. The RAM is a storage section which temporarily stores control data, etc. used for various control processes.

The Rpvs computation section 51 computes the internal resistance Rpvs of the pump cell 14 on the basis of the response signal Vs2 and the sensor output signal Vs1 notified from the AD conversion section 31. For example, the Rpvs computation section 51 computes the internal resistance Rpvs by dividing the difference between the response signal Vs2 and the sensor output signal Vs1 by the pulse current Irpvs (the internal resistance Rpvs=(Vs2−Vs1)/Irpvs).

The heater controlled variable computation section 53 digitally computes the temperature of the gas sensor 8 (specifically, the pump cell 14 of the sensor element 9) on the basis of the internal resistance Rpvs computed at the Rpvs computation section 51, and computes a heater heat generation amount which is necessary to make the computed temperature approach the sensor target temperature or maintain the computed temperature at the sensor target temperature. The heater controlled variable computation section 53 computes the duty ratio of the power supplied to the heater 26 on the basis of the computed heater heat generation amount, and generates a PWM control signal corresponding to the duty ratio.

Notably, a predetermined value is stored in the storage section (ROM, RAM, etc.) as a sensor target temperature. The heater controlled variable computation section 53 generates the PWM control signal through utilization of the sensor target temperature read out from the storage section.

By use of the power supplied from a power supply apparatus 59, the heater driver 57 energizes the heater 26, while controlling the energization on the basis of the PWM control signal from the heater controlled variable computation section 53. Thus, the heater 26 produces heat which is necessary to make the temperature of the gas sensor 8 approach the sensor target temperature or maintain the temperature of the gas sensor 8 at the sensor target temperature.

The pump current terminal 61 and the detection voltage terminal 63 are connected to one of the paired porous electrodes 16 (hereinafter referred to as the first porous electrode 16) of the pump cell 14 of the sensor element 9, and the reference potential terminal 65 is connected to the other of the paired porous electrodes 16. Within the gas detection apparatus 3, the pump current terminal 61 is connected to a connection path extending between the detection voltage terminal 63 and the sensor element 9 (the first porous electrode 16), whereby the pump current terminal 61 is electrically connected to the first porous electrode 16.

The terminal monitoring section 67 detects the potentials (analog values) of the pump current terminal 61, the detection voltage terminal 63, and the reference potential terminal 65, performs AD conversion for the detected potentials, and sends digital values representing the potentials to the anomaly detection section 69.

The anomaly detection section 69 determines whether or not each of the potentials of the pump current terminal 61, the detection voltage terminal 63, and the reference potential terminal 65 falls within a predetermined normal range, and determines that a terminal whose potential has deviated from the normal range is in an anomalous state. For example, when a wiring anomaly (short-to-ground anomaly) in which a terminal is electrically connected to the ground potential GND by mistake or a wiring anomaly (short-to-battery anomaly) in which a terminal is electrically connected to the power supply apparatus 59 by mistake occurs, the potential of that terminal deviates from the normal range.

Namely, the anomaly detection section 69 is configured to detect control anomalies, including at least a wiring anomaly at the wiring lines which connect the current DA conversion section 35, the current supply section 42, and the reference potential generation section 46 to the sensor element 9, on the basis of the potentials of the respective terminals (the pump current terminal 61, the detection voltage terminal 63, and the reference potential terminal 65). In the case where the anomaly detection section 69 has determined that at least one of the terminals is in the anomalous state, the anomaly detection section 69 sends anomaly information signal, including information of the terminal determined to be in an anomalous state, to the PID computation section 33, the heater controlled variable computation section 53, etc.

Upon receipt of the anomaly information signal, the PID computation section 33 and the heater controlled variable computation section 53 execute anomaly coping processes in accordance with the anomaly information signal. For example, the PID computation section 33 executes, as an anomaly coping process, a process of stopping the energization of the pump cell 14. The heater controlled variable computation section 53 executes, as an anomaly coping process, a process of decreasing the electric power supplied to the heater 26 (in other words, the duty ratio of the voltage applied to the heater).

Also, in the case where there exists a terminal determined to be in an anomalous state, the anomaly detection section 69 sends the anomaly information signal, including information of the terminal determined to be in an anomalous state, to the engine control apparatus 7 through the communication processing section 71. When the engine control apparatus 7 receives the gas detection signal S2 output from the sensor control apparatus 5 in a period during which the engine control apparatus 7 receives the anomaly information signal, the engine control apparatus 7 determines that the gas detection signal S2 is not normal but is anomalous and executes a concentration detection process in such a manner that the gas detection signal S2 is not used for detection of the oxygen concentration. As a result, the engine control apparatus 7 can prevent a decrease in the accuracy in detecting the oxygen concentration on the basis of the gas detection signal S2 from the sensor control apparatus 5.

The reference current generation section 73 is configured to generate a reference current Iref through use of the reference resistor 75. Specifically, the reference current generation section 73 detects a current which flows through the reference resistor 75 upon application of a predetermined reference voltage Vst (for example, 3.3 V) to the reference resistor 75, and generates the reference current Iref which is equal to the detected current. The reference current generation section 73 supplies the reference current Iref to control current generation sections of the sensor control apparatus 5 (the current DA conversion section 35, the current supply section 42, etc.) which output various currents.

The reference resistor 75 is composed of a resistor element having a predetermined reference resistance Rst (for example, 10 kΩ). Therefore, the detected reference current Iref assumes a fixed value determined by the reference voltage Vst and the reference resistance Rst (Iref=Vst/Rst).

Each of the control current generation sections of the sensor control apparatus 5 (the current DA conversion section 35, the current supply section 42, etc.) sets the current value of current output therefrom while using, as a reference, the current value of the reference current Iref received from the reference current generation section 73. For example, the current DA conversion section 35 sets the current value of the pump current Ip (which is an analog value) to a current value obtained by multiplying the current value of the reference current Iref by a predetermined integer. The current supply section 42 sets each of various current values, such as the pulse current Irpvs, to a current value obtained by multiplying the current value of the reference current Iref by a predetermined integer.

The current anomaly determination section 77 is configured to determine whether or not the reference current Iref output from the reference current generation section 73 has a normal value. The current anomaly determination section 77 can detect various current values such as the current value of the pump current Ip output from the current DA conversion section 35, the current value of the pulse current Irpvs output from the current supply section 42.

1-3. Current Anomaly Determination Section

The current anomaly determination section 77 executes a current anomaly determination process of determining whether or not the reference current Iref output from the reference current generation section 73 has a normal value. The current anomaly determination process executed by the current anomaly determination section 77 will be described with reference to the flowchart of FIG. 2.

Figure 2:
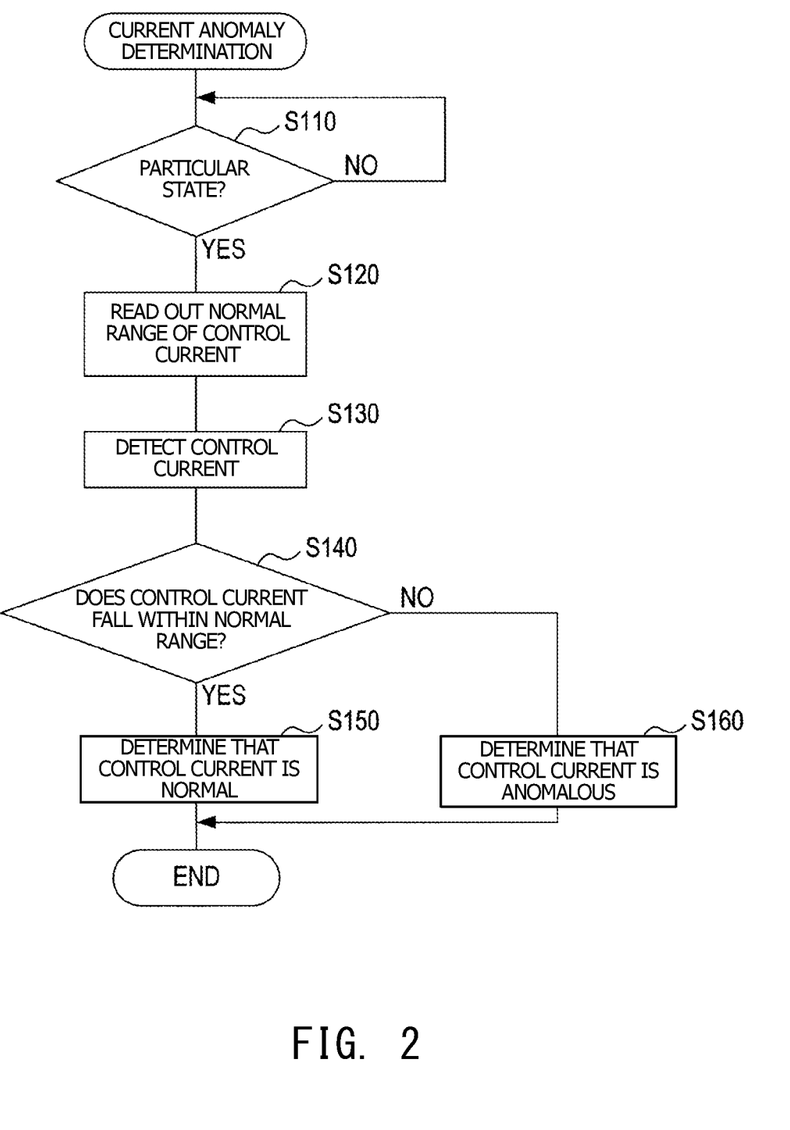
FIG. 2 is a flowchart representing the details of a current anomaly determination process.

After the sensor control apparatus 5 is started, the current anomaly determination section 77 executes the current anomaly determination process at predetermined execution intervals (for examples, intervals of 1 min).

First, in S110 (S stands for "step"), the current anomaly determination section 77 executing the current anomaly determination process determines whether or not there is established a particular state in which the determination as to whether or not the reference current Iref has a normal value can be made. In the case where the current anomaly determination section 77 makes a "Yes" determination, it proceeds to S120. In the case where the current anomaly determination section 77 makes a "No" determination, it waits until the particular state is established by repeatedly executing the above-mentioned step. In the present embodiment, when the operation state of the internal combustion engine is a fuel-cut state, the current anomaly determination section 77 determines that the particular state is established. The current anomaly determination section 77 determines the operation state of the internal combustion engine on the basis of operation state information received from the engine control apparatus 7.

After having made a "Yes" determination in S110 and proceeded to S120, the current anomaly determination section 77 reads out from the storage section (ROM, RAM, etc.) a normal range of the control current (the pump current Ip) output from the current DA conversion section 35 at the time of fuel cut. Notably, information regarding the normal range of the pump current Ip is stored in the storage section in advance. In the present embodiment, the normal range of the pump current Ip at the time of fuel cut is "a current range of not less than 1.33 mA." Namely, the current anomaly determination section 77 executing S120 sets the normal current range used for a determination process in S140 on the basis of the operation state of the internal combustion engine (the fuel cut state in the present embodiment).

The current anomaly determination section 77 executing S130 subsequent to S120 detects the control current (the pump current Ip) output from the current DA conversion section 35.

At the time of fuel cut, the oxygen concentration in the exhaust gas increases. Therefore, the pump current Ip has a value of 1.33 mA or greater "in the case where the reference current generation section 73 operates normally, the resistance of the reference resistor 75 is properly set, the connection state of the reference resistor 75 is proper, and the current DA conversion section 35 is normal." Meanwhile, the pump current Ip has a value of less than 1.33 mA "in the case where there has occurred some sort of anomaly such as failure of the reference current generation section 73, erroneous setting of the resistance of the reference resistor 75, connection anomaly of the reference resistor 75, or failure of the current DA conversion section 35."

The current anomaly determination section 77 executing S140 subsequent to S130 determines whether or not the control current detected in S130 falls within the normal current range read out in S120. When the current anomaly determination section 77 makes a "Yes" determination, it proceeds to S150. When the current anomaly determination section 77 makes a "No" determination, it proceeds to S160.

The current anomaly determination section 77 executing S150 determines that the reference current Iref has a normal value. Namely, the current anomaly determination section 77 determines that the reference current generation section 73 operates normally, the resistance of the reference resistor 75 is properly set, and the connection state of the reference resistor 75 is proper.

The current anomaly determination section 77 executing S160 determines that the reference current Iref has an anomalous value and that at least one of the reference resistor 75, the reference current generation section 73, and the current DA conversion section 35 is in an anomalous state. For example, the current anomaly determination section 77 determines that there has occurred some sort of anomaly such as failure of the reference current generation section 73, erroneous setting of the resistance of the reference resistor 75, connection anomaly of the reference resistor 75, or failure of the current DA conversion section 35.

After completion of S150 or S160, the current anomaly determination section 77 ends the current anomaly determination process.

When the internal combustion engine is in a particular operation state (fuel cut state), the current anomaly determination section 77 executing the current anomaly determination process detects the pump current Ip and determines whether or not the reference current Iref has a normal value by determining whether or not the detected pump current Ip falls within the normal current range.

For example, in the case where the state of connection between the reference current generation section 73 and the reference resistor 75 is an anomalous state (wire breakage anomaly, short-circuit anomaly, etc.), since the reference current generation section 73 and the reference resistor 75 each enter an anomalous state, the reference current Iref having an appropriate current value (in other words, a current value within the normal range) cannot be generated. In this case, since the pump current Ip is generated by the current DA conversion section 35 on the basis of the reference current Iref having an inappropriate current value, the pump current Ip has an inappropriate current value and deviates from the normal current range. Also, in the case where the reference current generation section 73 is normal and can generate the reference current Iref having an appropriate current value but the current DA conversion section 35 is in an anomalous state, the pump current Ip may have an inappropriate current value and deviate from the normal current range.

In the case where such an anomaly occurs, the current anomaly determination section 77 can determine whether or not the pump current Ip detected when the internal combustion engine is in the fuel cut state falls within the normal range and can determine, on the basis of the results of the determination, that the reference current Iref has an anomalous value and that at least one of the reference resistor 75, the reference current generation section 73, and the current DA conversion section 35 is in an anomalous state.

1-4. Effects

As described above, the sensor control apparatus 5 in the gas detection system 1 of the present embodiment includes the reference current generation section 73, the current DA conversion section 35, the current supply section 42, the reference resistor 75, and the current anomaly determination section 77.

The reference current generation section 73 is configured to generate the reference current Iref by using the reference resistor 75. The current DA conversion section 35 and the current supply section 42 are configured to generate control currents having predetermined current values (the pump current Ip and the pulse current Irpvs) while using the current value of the reference current Iref as a reference and supply the control currents to the sensor element 9 (the pump cell 14).

The current anomaly determination section 77 compares the normal current range within which the pump current Ip (control current) falls at the time of fuel cut (when the internal combustion engine is in the fuel cut state) with the pump current Ip which is generated by the current DA conversion section 35 at the time of fuel cut (S140). In the case where the pump current Ip has deviated from the normal current range ("No" determination in S140), the current anomaly determination section 77 determines that at least one of the reference resistor 75, the reference current generation section 73, and the current DA conversion section 35 is in an anomalous state (S160).

Namely, when the internal combustion engine is in the fuel cut state, the current anomaly determination section 77 compares the normal current range of the pump current Ip with the pump current Ip generated by the current DA conversion section 35. Thus, the current anomaly determination section 77 can determine that at least one of the reference resistor 75, the reference current generation section 73, and the current DA conversion section 35 is in an anomalous state in the case where the pump current Ip has deviated from the normal current range.

Since the sensor control apparatus 5 includes the current anomaly determination section 77 as described above, the sensor control apparatus 5 can determine an anomaly of at least one of the reference resistor 75, the reference current generation section 73, and the current DA conversion section 35.

The control target of the sensor control apparatus 5 is the gas sensor 8 (the sensor element 9) provided for the internal combustion engine, and the sensor control apparatus 5 includes the current anomaly determination section 77 (S120) which sets the normal current range on the basis of the operation state (fuel cut state) of the internal combustion engine.

Since the sensor control apparatus 5 includes such a current anomaly determination section 77, the sensor control apparatus 5 can set the normal current range in a particular operation state (fuel cut state) and can determine that the sensor control apparatus 5 itself is anomalous in the case where the particular control current (the pump current Ip) has deviated from the normal current range.

The sensor control apparatus 5 includes not only the control current generation sections (the current DA conversion section 35, the current supply section 42, etc.), the reference resistor 75, and the reference current generation section 73, but also the current anomaly determination section 77. Namely, the current anomaly determination section 77 is integrated with the control current generation sections (the current DA conversion section 35, the current supply section 42, etc.), the reference resistor 75, and the reference current generation section 73.

Since the sensor control apparatus 5 has a configuration in which the current anomaly determination section 77 is integrated with the control current generation sections, etc., the sensor control apparatus 5 can reliably determine whether or not an anomaly is present in the control current generation sections, etc. Therefore, the sensor control apparatus 5 can prevent the control current generation sections from supplying control currents while being in an anomalous state.

1-5. Correspondence Between Terms in Embodiment and Terms in Claims

A description will be given of the correspondence between terms used in the present embodiment and terms used in the claims.

The sensor control apparatus 5 corresponds to an example of the current control apparatus in the claims and corresponds to an example of the anomaly determination apparatus integrated with the current control apparatus in the claim. The gas sensor 8 (the sensor element 9) corresponds to an example of the control target in the claims; and the reference resistor 75 corresponds to an example of the reference resistor in the claims. The gas detection system 1 corresponds to an example of the control system in the claims.

The reference current generation section 73 corresponds to an example of the reference current generation section in the claims; each of the current DA conversion section 35 and the current supply section 42 corresponds to an example of the control current generation section in the claims; the current anomaly determination section 77 corresponds to an example of the current anomaly determination section in the claims; and the current anomaly determination section 77 executing S120 corresponds to an example of the range setting section in the claims.

2. Second Embodiment

2-1. Overall Configuration

Figure 3:
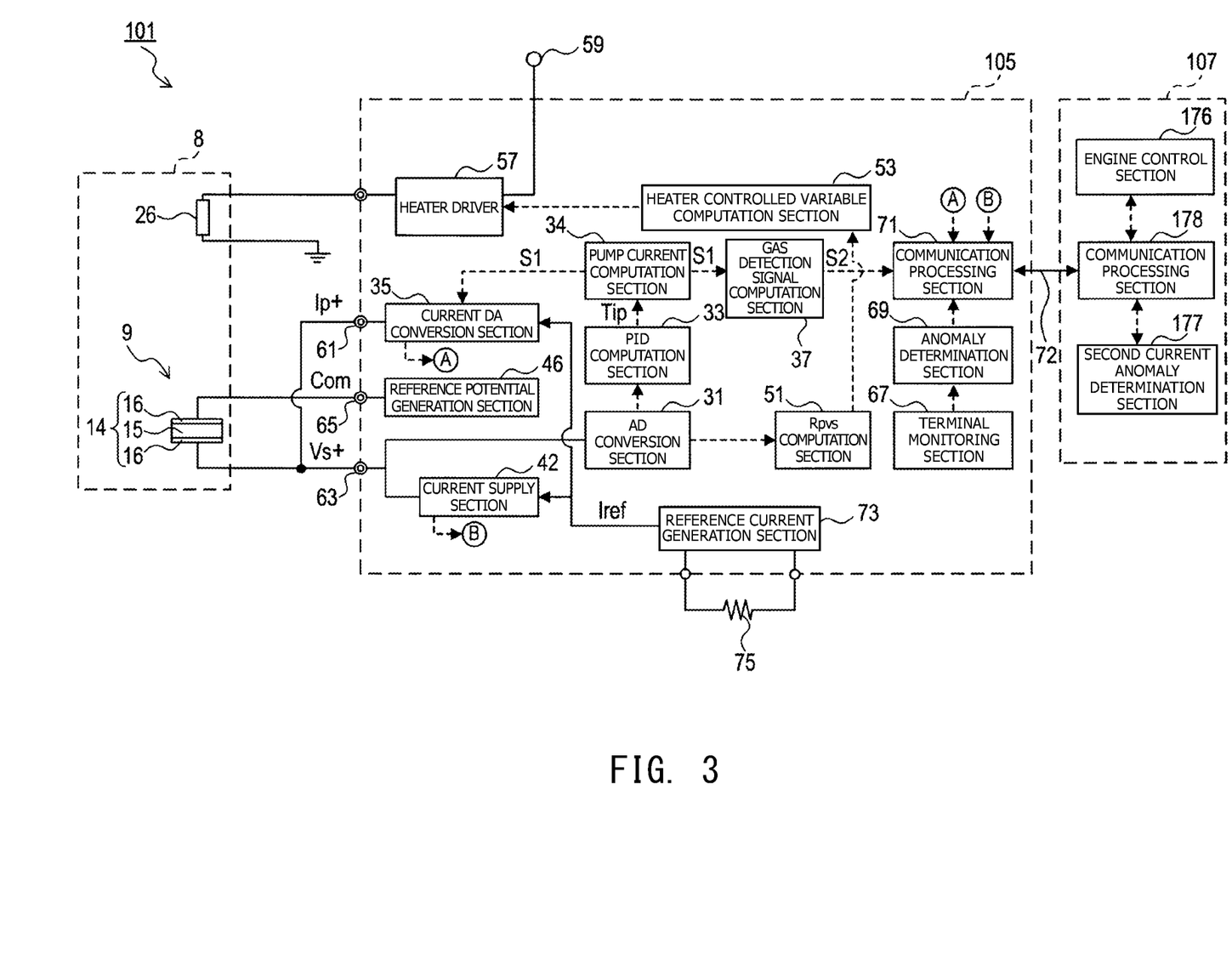
FIG. 3 is an overall diagram of a second gas detection system including a second sensor control apparatus and a second engine control apparatus.

As a second embodiment, there will be described a second gas detection system 101 in which an anomaly determination apparatus (a second engine control apparatus 107) is provided separately from a current control apparatus (a second sensor control apparatus 105).

FIG. 3 is an overall block diagram of the second gas detection system 101 of the present disclosure.

The second gas detection system 101 is used, for example, for the purpose of detecting a particular gas (oxygen in the present embodiment) contained in exhaust gas discharged from an internal combustion engine. The second gas detection system 101 includes the gas sensor 8, the second sensor control apparatus 105, and the second engine control apparatus 107.

Although the gas sensor 8 of the second gas detection system 101 has the same structure as the gas sensor 8 of the above-described gas detection system 1, the remaining constituent elements of the second gas detection system 101 differ from those of the above-described gas detection system 1 of the first embodiment. Therefore, in the following description, constituent elements of the second gas detection system 101 differing from those of the gas detection system 1 of the first embodiment will be mainly described. Also, the constituent elements of the second gas detection system 101 of the second embodiment which are identical with those of the gas detection system 1 of the first embodiment are denoted by the same reference numerals. The second sensor control apparatus 105 partially differs in configuration from the sensor control apparatus 5, and the second engine control apparatus 107 partially differs in configuration from the engine control apparatus 7.

The second sensor control apparatus 105 partially differs in configuration from the sensor control apparatus 5; namely, the second sensor control apparatus 105 differs from the sensor control apparatus 5 at least in the point that the current anomaly determination section 77 is not provided in the second sensor control apparatus 105. Also, the second sensor control apparatus 105 is configured such that various pieces of information sent from the communication processing section 71 to the second engine control apparatus 107 contain various current values, such as the current value of the pump current Ip output from the current DA conversion section 35 and the current value of the pulse current Irpvs output from the current supply section 42.

The second engine control apparatus 107 is a microcontroller which executes various control processes for controlling the internal combustion engine. The second engine control apparatus 107 includes a microcomputer. The microcomputer includes a CPU, a ROM, a RAM, and a signal input/output section. The various functions of the second engine control apparatus 107 are realized by a program which is stored in a non-transitory tangible recording medium and executed by the CPU. In this example, the ROM corresponds to the non-transitory tangible recording medium storing the program. Also, a method corresponding to the program is performed as a result of execution of the program. The signal input/output section sends various signals to external devices and receives various signals therefrom. Notably, the microcomputer may include a single CPU or a plurality of CPUs, a single ROM or a plurality of ROMs, a single RAM or a plurality of RAMs, and a single signal input/output section or a plurality of signal input/output sections. Also, some or all of the functions of the microcomputer may be realized by hardware; for example, by a single IC or a plurality of ICs. In FIG. 3, the second engine control apparatus 107 is shown in the form of a functional block diagram.

The second engine control apparatus 107 includes an engine control section 176, a second current anomaly determination section 177, and a communication processing section 178.

The communication processing section 178 executes a communication control process for sending various pieces of information to the second sensor control apparatus 105 (specifically, the communication processing section 71) and receiving various pieces of information therefrom by means of communication through the SPI communication line 72. The communication processing section 71 and the communication processing section 178 exchange information, including at least control information regarding the sensor control, through transmission and reception of the information. For example, the communication processing section 178 is configured to receive from the second sensor control apparatus 105 the gas detection signal S2 and various current values (the current values of the pump current Ip, the pulse current Irpvs, etc.).

As one of the various control processes for controlling the internal combustion engine, the engine control section 176 performs air-fuel ratio control for the internal combustion engine by using the oxygen concentration detected by the second sensor control apparatus 105 (specifically, the gas detection signal S2). The engine control section 176 computes the concentration of a particular gas (oxygen in the present embodiment) in the exhaust gas on the basis of the gas detection signal S2. Namely, the engine control section 176 computes the concentration of oxygen contained in the object gas on the basis of history data of the pump current Ip caused to flow through the pump cell 14 such that the oxygen concentration within the measurement chamber becomes equal to a predetermined target concentration (for example, an oxygen concentration corresponding to the stoichiometric air-fuel ratio).

The second current anomaly determination section 177 is configured to determine whether or not the reference current Iref output from the reference current generation section 73 in the second sensor control apparatus 105 has an appropriate value on the basis information received through the SPI communication line 72. The second current anomaly determination section 177 is configured such that it can receive various current values, such as the current value of the pump current Ip output from the current DA conversion section 35 and the current value of the pulse current Irpvs output from the current supply section 42, through the communication processing section 178.

Like the current anomaly determination section 77 of the first embodiment, the second current anomaly determination section 177 executes a current anomaly determination process for determining whether or not the reference current Iref output from the reference current generation section 73 has a normal value.

Notably, the current anomaly determination process executed by the second current anomaly determination section 177 partially differs from that executed by the current anomaly determination section 77. For example, the second current anomaly determination section 177 receives from the engine control section 176 the operation state of the internal combustion engine used for the determination in S110. At the time of execution of S120, the second current anomaly determination section 177 reads out from the storage section (ROM, RAM, etc.) of the second engine control apparatus 107 the normal range of the control current (the pump current Ip) output from the current DA conversion section 35 at the time of fuel cut. Notably, the information regarding the normal range of the pump current Ip is stored in the storage section of the second engine control apparatus 107 in advance. The second current anomaly determination section 177 executing S130 receives, through the communication processing section 178, the control current (the pump current Ip) output from the current DA conversion section 35.

The processing details of S140 to S160 in the second current anomaly determination section 177 are identical with those in the current anomaly determination section 77.

When the internal combustion engine is in a particular operation state (fuel cut state), like the current anomaly determination section 77, the second current anomaly determination section 177 executing such a current anomaly determination process detects the pump current Ip and determines whether or not the reference current Iref has a normal value by determining whether or not the detected pump current Ip falls within the normal range.

Therefore, on the basis of the results of the determination as to whether or not the pump current Ip detected when the internal combustion engine is in the fuel cut state falls within the normal range, the second current anomaly determination section 177 can determine that the reference current Iref has an anomalous value and determine that at least one of the reference resistor 75, the reference current generation section 73, and the current DA conversion section 35 is in an anomalous state.

2-2. Effects

As described above, in the second gas detection system 101 of the second embodiment, the second sensor control apparatus 105 includes the reference current generation section 73, the current DA conversion section 35, the current supply section 42, the reference resistor 75, and the communication processing section 71, and the second engine control apparatus 107 includes the second current anomaly determination section 177 and the communication processing section 178.

The second current anomaly determination section 177 compares the normal current range within which the pump current Ip (control current) falls at the time of fuel cut (when the internal combustion engine is in the fuel cut state) with the pump current Ip which is generated by the current DA conversion section 35 at the time of fuel cut (S140). In the case where the pump current Ip has deviated from the normal current range ("No" determination in S140), the second current anomaly determination section 177 determines that at least one of the reference resistor 75, the reference current generation section 73, and the current DA conversion section 35 is in an anomalous state (S160).

Namely, when the internal combustion engine is in the fuel cut state, the second current anomaly determination section 177 compares the normal current range of the pump current Ip with the pump current Ip generated by the current DA conversion section 35. Thus, the second current anomaly determination section 177 can determine that at least one of the reference resistor 75, the reference current generation section 73, and the current DA conversion section 35 is in an anomalous state in the case where the pump current Ip has deviated from the normal current range.

Since the second engine control apparatus 107 includes the second current anomaly determination section 177, the second engine control apparatus 107 can determine an anomalous state of the second sensor control apparatus 105 (an anomaly of at least one of the reference resistor 75, the reference current generation section 73, and the current DA conversion section 35).

The control target of the second sensor control apparatus 105 is the gas sensor 8 (the sensor element 9) provided for the internal combustion engine, and the second engine control apparatus 107 includes the second current anomaly determination section 177 (S120) which sets the normal current range on the basis of the operation state (fuel cut state) of the internal combustion engine.

Since the second engine control apparatus 107 includes such a second current anomaly determination section 177, the second engine control apparatus 107 can set the normal current range in a particular operation state (fuel cut state) and can determine that the second sensor control apparatus 105 is anomalous in the case where the particular control current (the pump current Ip) has deviated from the normal current range.

The second engine control apparatus 107 is provided separately from the second sensor control apparatus 105 and includes the second current anomaly determination section 177 and the communication processing section 178. The communication processing section 178 is configured to receive information regarding the particular control current (the pump current Ip, etc.) from the second sensor control apparatus 105. The second current anomaly determination section 177 is configured to perform the determination on the basis of the information received by the communication processing section 178.

As described above, even in the case where the second engine control apparatus 107 having the second current anomaly determination section 177 is provided separately from the second sensor control apparatus 105, the second engine control apparatus 107 can determine whether or not an anomaly has occurred in the second sensor control apparatus 105, because the second engine control apparatus 107 includes the communication processing section 178. Therefore, through use of the second engine control apparatus 107, it is possible to prevent the second sensor control apparatus 105 from supplying the control currents (the pump current Ip, etc.) to the gas sensor 8 while being in the anomalous state.

The second gas detection system 101 includes the second engine control apparatus 107 and the second sensor control apparatus 105, and the second engine control apparatus 107 includes the second current anomaly determination section 177.

In the second gas detection system 101 as described above, the second engine control apparatus 107 is configured to determine whether or not an anomaly has occurred in the second sensor control apparatus 105. Therefore, it is possible to prevent the second sensor control apparatus 105 from supplying the control currents (the pump current Ip, etc.) to the gas sensor 8 while being in the anomalous state.

2-3. Correspondence Between Terms in Second Embodiment and Terms in Claims

A description will be given of the correspondence between terms used in the second embodiment and terms used in the claims.

The second sensor control apparatus 105 corresponds to an example of the current control apparatus in the claims; and the second engine control apparatus 107 corresponds to an example of the anomaly determination apparatus in the claim. The gas sensor 8 (the sensor element 9) corresponds to an example of the control target in the claims; and the reference resistor 75 corresponds to an example of the reference resistor in the claims. The second gas detection system 101 corresponds to an example of the control system in the claims.

The reference current generation section 73 corresponds to an example of the reference current generation section in the claims; each of the current DA conversion section 35 and the current supply section 42 corresponds to an example of the control current generation section in the claims; the second current anomaly determination section 177 corresponds to an example of the current anomaly determination section in the claims; the second current anomaly determination section 177 executing S120 corresponds to an example of the range setting section in the claims; and the communication processing section 178 corresponds to an example of the information receiving section in the claims.

3. Other Embodiments

Although embodiments of the present invention has been described, the present invention is not limited to the above-described embodiments, and the present invention can be implemented in various forms without departing from the scope of the present invention.

In the anomaly determination apparatuses (the sensor control apparatus 5 and the second engine control apparatus 107) of the above-described embodiments, the particular state is the fuel cut state of the internal combustion engine and the particular state quantity is the particular control current (the pump current Ip). However, the anomaly determination apparatus of the present disclosure is not limited to such embodiments. For example, the anomaly determination apparatuses may be configured such that the particular state is "a state in which the element temperature of the gas sensor 8 (specifically, the sensor element 9) becomes a particular temperature," and the particular state quantity is "the internal resistance Rpvs of the pump cell 14 detected on the basis of the pulse current Irpvs output from the current supply section 42." Specifically, the particular state quantity may be the internal resistance Rpvs determined on the basis of the pulse current Irpvs at the time when the element temperature of the sensor reaches a predetermined temperature after elapse of a sufficiently long sensor heating time from the startup.

As described above, the internal resistance Rpvs is a state quantity computed through use of the sensor output signal Vs1, the response signal Vs2, and the pulse current Irpvs (Rpvs=(Vs2−Vs1)/Irpvs). Namely, the internal resistance Rpvs is a state quantity which changes with the control current (the pulse current Irpvs) supplied by the current supply section 42 or the control current (the pump current Ip) supplied by the current DA conversion section 35. Notably, the sensor output signal Vs1 is a state quantity which changes with the pump current Ip, and the response signal Vs2 is a state quantity which changes with the pulse current Irpvs. Therefore, when the reference current Iref has an inappropriate value, the control currents (the pulse current Irpvs and the pump current Ip) may have inappropriate values, and the internal resistance Rpvs may have an inappropriate value (a value different from a value corresponding to the actual temperature of the sensor element 9).

Therefore, the determination as to whether or not the sensor control apparatus is in an anomalous state can be made as follows. A particular internal resistance Rpvs which is the internal resistance Rpvs at the time when the internal combustion engine is in an operation state in which the element temperature of the sensor element 9 becomes the particular temperature is detected. The detected particular internal resistance Rpvs is compared with a normal numerical range within which the value of the particular internal resistance Rpvs falls when the element temperature of the sensor element 9 is the particular temperature. The determination as to whether or not the sensor control apparatus is in an anomalous state is made on the basis of the results of the comparison. In this case, in S110, the current anomaly determination section executing the current anomaly determination process determines whether or not the internal combustion engine is in an operation state in which the element temperature of the sensor element 9 becomes the particular temperature. Also, in S120, the current anomaly determination section reads out the normal numerical range within which the value of the particular internal resistance Rpvs falls when the element temperature of the sensor element 9 is the particular temperature. In S130, the current anomaly determination section detects the particular internal resistance Rpvs by using the Rpvs computation section 51. In S140, the current anomaly determination section determines whether or not the value of the particular internal resistance Rpvs falls within the normal numerical range. When the current anomaly determination section makes a "Yes" determination, it proceeds to S150 and determines that the sensor control apparatus is in a normal state. When the current anomaly determination section makes a "No" determination, it proceeds to S160 and determines that the sensor control apparatus is in an anomalous state.

When the element temperature of the sensor element 9 becomes a particular temperature, the anomaly determination apparatus having the configuration described above compares the particular internal resistance Rpvs detected by the Rpvs computation section 51 with the normal numerical range within which the value of the particular internal resistance Rpvs falls. Thus, the anomaly determination apparatus can determine that at least one of the reference resistor 75, the reference current generation section 73, and the current DA conversion section 35 is in an anomalous state in the case where the value of the particular internal resistance Rpvs has deviated from the normal numerical range. Therefore, such an anomaly determination apparatus determines an anomaly of at least one of the reference resistor 75, the reference current generation section 73, and the current DA conversion section 35 by performing the above-described determination.

Notably, the anomaly determination performed through use of the internal resistance Rpvs may be applied to either one of the first embodiment and the second embodiment.

The particular state is not limited to the above-described particular state. For example, the particular state may be a state in which the anomaly determination apparatus is inspected before shipment. In the case where the particular state is the state in which the anomaly determination apparatus is inspected before shipment, the anomaly determination may be performed by setting beforehand the current value (current value for inspection) of the control current which is output from the control current generation section of the current control apparatus during the inspection before shipment, and comparing the control current (the particular control current) output during the inspection before shipment with the normal current range. The normal current range in this case may be a numeral range determined by using the current value for inspection as the center value and taking an allowable error into account.

Also, in the case where the particular state is the state in which the anomaly determination apparatus is inspected before shipment, the anomaly determination may be performed as follows. Instead of the sensor element, a resistor for inspection which has a predetermined resistance (hereinafter also referred to as the prescribed resistance) is connected to the current control apparatus. During the inspection before shipment, the resistance of the resistor for inspection is detected as the internal resistance of the sensor element (hereinafter, the resistance of the resistor will also be referred to as the detected resistance), and the detected resistance is compared with a normal numerical range. The normal numerical range in this case may be a numeral range determined by using the prescribed resistance as the center value and taking an allowable error into account.

In the current anomaly determination processes of the above-described embodiments, one particular state is used for the anomaly determination. However, the current anomaly determination processes are not limited to such an embodiment. For example, each of the current anomaly determination processes may be a current anomaly determination process which selects one of a plurality of particular states, and performs the anomaly determination on the basis of the particular state quantity detected in the selected particular state. Specifically, each of the current anomaly determination processes may be a current anomaly determination process which allows a user of the anomaly determination apparatus to select either one of the operation state (fuel cut state) of the internal combustion engine and the inspection before shipment as a particular state and performs the anomaly determination on the basis of the results of comparison between the normal numerical range and the particular state quantity (the pump current Ip, the internal resistance Rpvs, etc.) detected in the particular state selected by the user.

Also, an anomaly determination apparatus which selects one of a plurality of particular states may be configured to appropriately set the normal numerical range in accordance with the type of the selected particular state. Since this configuration allows appropriate setting of the normal numerical range in accordance with various particular states, an anomaly of the current control apparatus can be determined properly.

In the above-described embodiments, the current control apparatus (the sensor control apparatus) supplies control currents to an element section (the sensor element 9) including a single cell (the pump cell 14) only. However, the configuration of the element section which is a control target is not limited to such a configuration, and the element section may include two or more cells. For example, the current control apparatus may be one which supplies control currents to an element section (two-cell-type element section) which includes, for example, a pump cell and an electromotive force cell (detection cell). In the case where a sensor including a two-cell-type element section and a heater section is controlled through use of the sensor control apparatus 5 or the second sensor control apparatus 105, the pump cell is connected between the pump current terminal 61 and the reference potential terminal 65, and the electromotive force cell (detection cell) is connected between the detection voltage terminal 63 and the reference potential terminal 65. Even in the current control apparatus (the sensor control apparatus) for such an application, the anomaly determination can be performed by use of the anomaly determination apparatus of the present disclosure.

Also, the timings of execution of the anomaly determination are not limited to the timings determined by the predetermined execution intervals as in the above-described embodiments, and the anomaly determination may be performed one time only at a particular timing, for example, a point in time after elapse of a predetermined time from startup.

The function of one component in the above embodiments may be distributed to a plurality of components, or the functions of a plurality of components may be realized by one component. Part of the configurations of the above embodiments may be omitted. At least part of the configuration of each of the above embodiments may be added to or partially replace the configurations of other embodiments. All modes included in the technical idea specified by the wording of the claims are embodiments of the present disclosure.

The present disclosure may be realized in various forms other than the above-described anomaly determination apparatus. For example, the present disclosure may be realized as a system including the anomaly determination apparatus as a component, a program for causing a computer to function as the anomaly determination apparatus, a non-transitory tangible recording medium, e.g., a semiconductor memory, in which the program is recorded, and an anomaly determination method.

DESCRIPTION OF REFERENCE NUMERALS

1 . . . gas detection system, 3 . . . gas detection apparatus, 5 . . . sensor control apparatus, 7 . . . engine control apparatus, 8 . . . gas sensor, 9 . . . sensor element, 14 . . . pump cell, 15 . . . solid electrolyte body, 16 . . . porous electrode, 26 . . . heater, 31 . . . AD conversion section (analog-to-digital conversion section), 33 . . . PID computation section, 34 . . . pump current computation section, 35 . . . current DA conversion section (current digital-to-analog conversion section), 37 . . . gas detection signal computation section, 42 . . . current supply section, 46 . . . reference potential generation section, 51 . . . Rpvs computation section, 53 . . . heater controlled variable computation section, 61 . . . pump current terminal (Ip+ terminal), 63 . . . detection voltage terminal (Vs+ terminal), 65 . . . reference potential terminal (COM terminal 65), 67 . . . terminal monitoring section, 69 . . . anomaly detection section, 71 . . . communication processing section, 72 . . . SPI communication line, 73 . . . reference current generation section, 75 . . . reference resistor, 77 . . . current anomaly determination section, 101 . . . second gas detection system, 105 . . . second sensor control apparatus, 107 . . . second engine control apparatus, 176 . . . engine control section, 177 . . . second current anomaly determination section, 178 . . . communication processing section.

The invention claimed is:

1. A current control apparatus for supplying a control current to a control target, said current control apparatus comprising:
a reference resistor;
a reference current generation section that generates a reference current by using the reference resistor;
a control current generation section that generates a control current having a predetermined current value while using a current value of the reference current as a reference and supplies the control current to the control target, and
a current anomaly determination section that compares a normal numerical range within which a state quantity changing with the control current falls in a particular state with a particular state quantity, which is the state quantity corresponding to the control current generated by the control current generation section in the particular state and determines that at least one of the reference resistor, the reference current generation section, and the control current generation section is in an anomalous state in the case where the particular state quantity has deviated from the normal numerical range.

2. The current control apparatus according to claim 1, further comprising a range setting section that sets the normal numerical range based on an operation state of an internal combustion engine, wherein
the control target is a sensor provided for the internal combustion engine.

3. A control system comprising:
a current control apparatus including a reference current generation section which generates a reference current by using a reference resistor, and a control current generation section which generates a control current having a predetermined current value while using a current value of the reference current as a reference and supplies the control current to the control target; and
a current anomaly determination section that compares a normal numerical range within which a state quantity changing with the control current falls in a particular state with a particular state quantity, which is the state quantity corresponding to the control current generated by the control current generation section in the particular state and determines that at least one of the reference resistor, the reference current generation section, and the control current generation section is in an anomalous state in the case where the particular state quantity has deviated from the normal numerical range.

4. The control system according to claim 3, wherein the current anomaly detection section is integrated with the current control apparatus.

5. The control system according to claim 3, wherein
the current anomaly detection section is provided separately from the current control apparatus and includes an information receiving section which receives information regarding the particular state quantity from the current control apparatus, and
the current anomaly determination section performs a determination based on the information received by the information receiving section.

* * * * *